United States Patent
Guracar

(10) Patent No.: US 10,856,851 B2
(45) Date of Patent: Dec. 8, 2020

(54) MOTION ARTIFACT SUPPRESSION FOR THREE-DIMENSIONAL PARAMETRIC ULTRASOUND IMAGING

(71) Applicant: Siemens Medical Solutions USA, Inc., Malvern, PA (US)

(72) Inventor: Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 312 days.

(21) Appl. No.: 15/980,110

(22) Filed: May 15, 2018

(65) Prior Publication Data

US 2018/0256133 A1    Sep. 13, 2018

Related U.S. Application Data

(63) Continuation of application No. 13/952,475, filed on Jul. 26, 2013, now Pat. No. 10,034,657.

(51) Int. Cl.
| | |
|---|---|
| *A61B 8/08* | (2006.01) |
| *G01S 7/52* | (2006.01) |
| *A61B 8/14* | (2006.01) |
| *A61B 8/06* | (2006.01) |

(52) U.S. Cl.
CPC ............ *A61B 8/5276* (2013.01); *A61B 8/483* (2013.01); *G01S 7/52095* (2013.01); *A61B 8/06* (2013.01); *A61B 8/0891* (2013.01); *A61B 8/145* (2013.01); *A61B 8/5207* (2013.01)

(58) Field of Classification Search
CPC ......... A61B 8/06; A61B 8/0891; A61B 8/145; A61B 8/483; A61B 8/5207; A61B 8/5276; G01S 7/52095
See application file for complete search history.

(56) References Cited

U.S. PATENT DOCUMENTS

| | | | |
|---|---|---|---|
| 4,448,200 A | 5/1984 | Brooks et al. | |
| 5,454,371 A | 10/1995 | Fenster et al. | |
| 5,876,342 A | 3/1999 | Chen et al. | |
| 6,014,473 A | 1/2000 | Hossack et al. | |
| 6,254,539 B1 | 7/2001 | Pang et al. | |
| 6,306,091 B1 | 10/2001 | Sumanaweera et al. | |
| 6,494,841 B1 | 12/2002 | Thomas et al. | |
| 6,602,195 B1 | 8/2003 | Krishnan et al. | |
| 6,632,177 B1 | 10/2003 | Phillips et al. | |
| 6,638,228 B1 | 10/2003 | Brock-Fisher et al. | |
| 6,682,482 B1 | 1/2004 | Krishnan | |
| 7,033,320 B2 | 4/2006 | Von Behren et al. | |
| 7,454,048 B2 | 11/2008 | Schoisswohl et al. | |
| 7,530,951 B2 | 5/2009 | Fehre et al. | |

(Continued)

OTHER PUBLICATIONS

N. G. Rognin et al., "Parametric Imaging for Characterizing Focal Liver Lesions in Contrast-Enhanced Ultrasound," IEEE Transactions on Ultrasonics, Ferroelectrics and Frequency Control, vol. 57, No. 11, pp. 2503-2511, Nov. 2010.

*Primary Examiner* — Amelie R Davis

(57) ABSTRACT

Motion artifacts are suppressed for three-dimensional parametric ultrasound imaging. Motion tracking is performed so that the parameter values derived over time are based on return from the same locations. Distortion due to the scan pattern is accounted for in the results of the motion tracking, such as by re-sampling the results to deal with discontinuity in time between data from adjacent sub-volumes and/or by aligning the scan pattern based on a direction of motion.

11 Claims, 7 Drawing Sheets

(56) References Cited

U.S. PATENT DOCUMENTS

| | | |
|---|---|---|
| 7,998,074 B2 | 8/2011 | Chomas et al. |
| 7,998,373 B2 | 8/2011 | Wakatake et al. |
| 2002/0082500 A1 | 6/2002 | Henderson et al. |
| 2003/0105401 A1 | 6/2003 | Jago et al. |
| 2005/0033123 A1 | 2/2005 | Gardner et al. |
| 2009/0069675 A1 | 3/2009 | Srinivasan |
| 2010/0185093 A1 | 7/2010 | Hamilton |
| 2010/0298706 A1 | 11/2010 | Averkiou et al. |
| 2011/0144495 A1 | 6/2011 | Wilkening et al. |
| 2012/0152021 A1 | 6/2012 | Ma et al. |
| 2013/0006108 A1 | 1/2013 | Yoshiara et al. |

MOTION ARTIFACT SUPPRESSION FOR THREE-DIMENSIONAL PARAMETRIC ULTRASOUND IMAGING

CROSS-REFERENCE TO RELATED APPLICATION

This application is a Continuation and claims benefit of priority under 35 USC § 120 to U.S. patent application Ser. No. 13/952,475, filed Jul. 26, 2013.

BACKGROUND

The present embodiments relate to artifact reduction in ultrasound imaging. In particular, artifacts from three-dimensional ultrasound imaging are reduced.

Three-dimensional perfusion parametric images of ultrasound contrast agents are useful for studying variations in blood flow in organs and tissues in response to disease states, drugs, or other physiological conditions. For volume perfusion parametric imaging, contrast agent is introduced into the bloodstream. A region is then imaged in a non-destructive contrast sensitive mode to measure a blood perfusion parameter, such as contrast agent arrival time, maximum intensity projection, normalized time integral, or maximum area coverage. Other types of parametric imaging where a characteristic of acoustic response over time is calculated are known.

For ultrasound imaging of a volume, different parts of the volume are scanned over time. However, if there is significant motion during consecutive acquisitions, then the values of the parameters may be based on returns from different locations rather than the same location. One way to avoid motion is to have the user hold their breath. Collecting sufficient data for parametric imaging may require the patient to hold their breath for too long. For example, contrast wash-in and wash-out takes place over 30 seconds to 4 minutes. The offset in data caused by breathing may be countered by motion tracking. However, motion tracking may be ineffective due to a low sampling rate of the volume. Beamformer data rates may be low, such as sub-Hertz. Improvements to beamformer data rates may permit volume rates on the order 5-10 Hertz, which is still too low for good quality tracking without significant geometric distortion.

BRIEF SUMMARY

By way of introduction, the preferred embodiments described below include methods, systems, computer readable media, and instructions for motion artifact suppression for three-dimensional parametric ultrasound imaging. Motion tracking is performed so that the parameter values derived over time are based on return from the same locations. Distortion due to the scan pattern is accounted for in the results of the motion tracking, such as by re-sampling the results to deal with discontinuity in time between data from adjacent sub-volumes and/or by aligning the scan pattern based on a direction of motion.

In a first aspect, a method is provided for motion artifact suppression for three-dimensional parametric ultrasound imaging. A volume of a patient is scanned with multi-beam reception where multi-beam groups progress in time along a first row in a first direction, then along a second row in the first direction. The first row is adjacent to the second row along a second direction. The spatially adjacent multi-beam groups of the different rows are scanned at non-adjacent times. The spatially adjacent multi-beam groups between the first and second rows are spatially registered. Parametric information is calculated from ultrasound data from the scanning. Contraction or dilation is accounted for in the calculating. The accounting is a function of the spatial registering. A parametric image representing the volume is generated. The parametric image is a function of the parametric information.

In a second aspect, a non-transitory computer readable storage medium has stored therein data representing instructions executable by a programmed processor for motion artifact suppression for three-dimensional parametric ultrasound imaging. The storage medium includes instructions for motion tracking for blocks of ultrasound data acquired with multiple beam reception in a volume scan, timing of the volume scan being different for blocks spaced in one direction than for blocks spaced in another direction, correcting for the timing being different for the directions, and displaying an image where the image is a function of the ultrasound data after the correcting.

In a third aspect, a method is provided for motion artifact suppression for three-dimensional parametric ultrasound imaging. A direction of movement of anatomy within a patient is detected. A transducer ultrasonically scans a volume with ultrasound in a pattern sweeping across rows of the volume in sequence. The pattern is aligned with the anatomy as a function of the direction of the movement of the anatomy.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Accurate volume scanning, even where motion occurs, is desired for parametric imaging, quantification and/or for multimodality volumetric registration (e.g., ultrasound registered with computed tomography or magnetic resonance data). To scan the volume, different slices or slabs of the volume are scanned in sequence. For example, multi-beam acquisition is swept along a row, then shifted to sweep along a different row, row after row. This acquisition pattern is used in combination with motion tracking for parametric imaging. The motion tracking allows for quantification over time with returns from the same locations. Motion tracking alone may be insufficient due to the interaction of the scan pattern with motion.

In one approach, motion in combination with the scan pattern is accounted for in the parametric imaging. The temporal acquisition pattern is accounted for with respect to the elevation scan direction (e.g., across rows). Re-sampling corrects for elevation contraction or dilation. Overlap and/or gaps created by motion tracking scan data acquired during motion are identified and dealt with.

In another approach, the volumetric acquisition scan pattern is altered in response to measured periodic breathing motion. The "fast time" scan direction (e.g., azimuth or along rows) is aligned to the predominant direction of motion. The result is less motion artifact along the "slow time" scan direction (e.g., across rows or elevation), resulting in little or no dilation or contraction.

Figure 1:
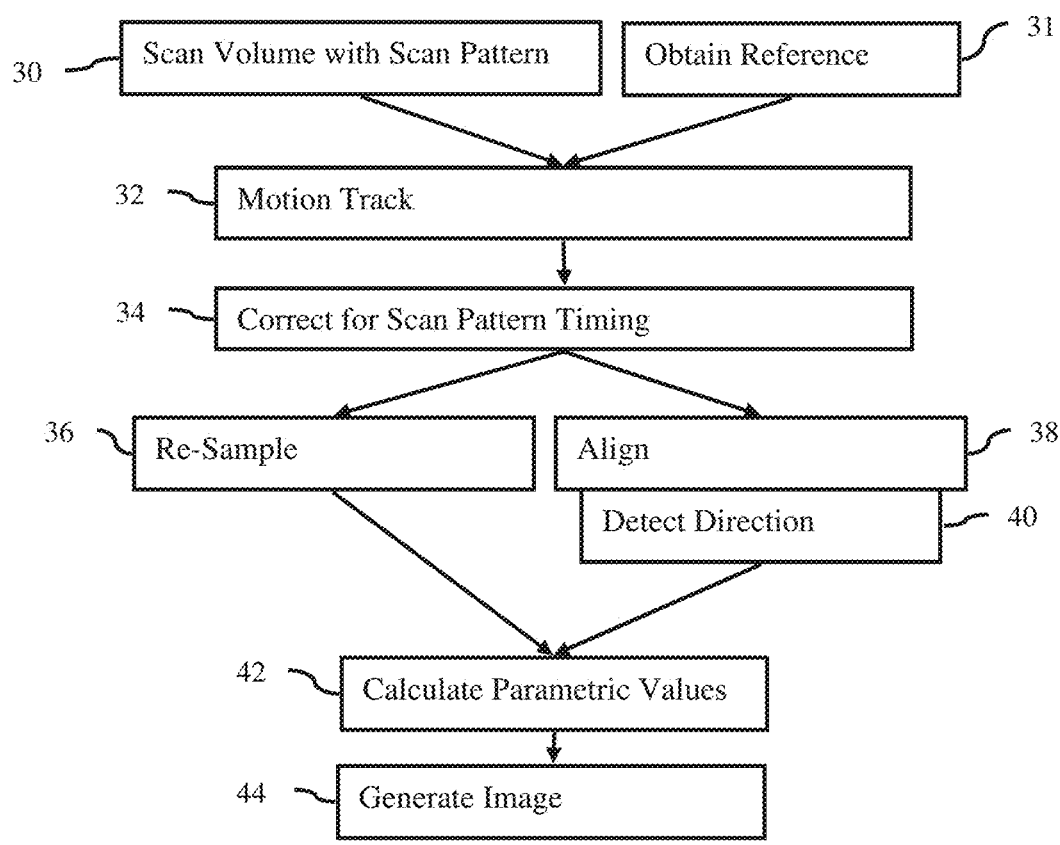
FIG. 1 is a flow chart diagram of one embodiment of a method for motion artifact suppression for three-dimensional parametric ultrasound imaging.

FIG. 1 shows one embodiment of a method for motion artifact suppression for three-dimensional parametric ultrasound imaging. The method is implemented by the system 10 of FIG. 8 or a different system. The method is performed in the order shown or a different order. Additional, different, or fewer acts may be provided. For example, act 36 is an alternative to acts 38, 40. As another example, act 42 is not performed, and the motion corrected volume is instead used for registering with a volume represented by data of a different imaging modality.

In act 30, ultrasound data representing a volume of a patient is obtained. In one embodiment, the ultrasound data represents reperfusion of contrast agents in the volume. A sequence of ultrasound frames of data is acquired. Each frame represents the entire volume. In one embodiment, the frames are generated after having destroyed contrast agents, before perfusion by contrast agents, or after full perfusion by contrast agents. The sequence is generated by acquiring frames of data with ultrasound. The ultrasound data is obtained in real-time or by acquiring previously generated frames of data (e.g., DICOM images). The sequence may be substantially continuous or periodic (e.g., acquired once or more every heart cycle). In alternative embodiments, only one or two frames are acquired.

The sequence includes frames of data representing the scanned volume at different times. Each frame of data represents a same or overlapping region. Some frames may represent slightly different regions, such as due to motion of the transducer or patient. A frame of data is a group of data representing a complete scan at a given time of a three-dimensional region. For example, a frame of data represents a conical, cuboid, or cylindrical region within the patient. The frame of data includes samples (e.g., voxels) of the volume.

The volume of the patient being scanned may include contrast agents or an area likely to include contrast agents after arrival of the agents. The contrast agents respond to ultrasound energies. Some or all of the frames of data include information from contrast agents. The information may also or alternatively include response from tissue or fluids. In one embodiment, the information is obtained at a cubic fundamental of ultrasound signals. For example, ultrasound signals are transmitted in a plurality of pulses having at least two different amplitude levels and phases. To avoid or minimize destruction of the contrast agents, low amplitude transmissions (e.g., MI less than 0.7) are used. Signals responsive to the transmissions are combined. Data is acquired at each spatial location of a region of interest in each frame of data. In other embodiments, strain, elasticity, or other non-contrast agent, parametric imaging is performed.

Only one type of data is represented in the frames of data, such as data representing just contrast agents or responses from contrast agent and tissue. Alternatively, the frames of data represent different types of data, such as in a same frame or in different sets of frames.

Each sequence lasts a period, such as 1-30 seconds. Two or more (e.g., tens or hundreds) frames are acquired in each sequence. The period may be based on the perfusion and/or wash out of contrast agents. For example, the sequence continues until a sufficient contrast agent response is obtained or ceases. An average return, or change in average return, area or volume of return, change in area or volume of contrast agent return or other indicator may be used to indicate sufficient perfusion or wash-out. User input may indicate completion of the period. The period may be based on a timer, such as a time set for 1-30 seconds.

To acquire a given frame of data representing the volume, the volume is scanned in segments. Within each of the different segments, data is obtained prior to obtaining data for the next segment. Ultrasound from a transducer is used to sequentially acquire data from different portions of the volume of the patient. The segments are different portions of the volume so represent the three-dimensional region of the patient in combination. The collection of measurements from a number of sub-volumes is combined to produce a full volume.

A multi-dimensional array of elements is used to scan the segments. The multi-dimensional array, such as a 2D array, is electronically steered in azimuth and elevation dimensions. Scan lines may be determined by delays and/or apodization. Ultrasound data is obtained using acoustic energy generated with electrical steering in azimuth and elevation directions. The steering directs the scan to sample within a given segment. The array may be moved or held in place. The steering allows scanning of different segments and different scan lines within a given segment.

In one embodiment, each segment corresponds to multi-beam reception. For a segment, one or more transmit beams covering the segment are formed. In response to each transmit beam, multiple receive beams are formed. For example, a region of 8×8 (e.g., azimuth and elevation) scan lines is scanned. A single transmit beam may be formed for receiving the 64 receive beams of the segment. Any number of receive beams may be formed in multi-beam scanning, such as four or more. The receive beams are formed simultaneously as a group representing the entire segment. In the 8×8 example above, the segment includes 64 scan lines and is defined by the multi-beam grouping. The collection of multi-beam receive lines are acquired simultaneously.

To scan the volume, the multi-beam approach is repeated for different segments. The scanning occurs in a scan pattern. The volume is acquired in a raster-type scan format, with a "fast" scan direction by convention in azimuth and the "slow" scan direction by convention in elevation. The segments or blocks are scanned in rows, such as sweeping the multi-beam groups along an azimuth direction for one row, then sweeping the multi-beam groups along the azimuth direction in an elevation adjacent azimuth extending row, and so on. For example, the volume is broken down into 16×16 segments in rows and columns. A given row may represent any number of elevation spaced receive beams (e.g., 8 in the 8×8 example). Any number of segments within a row may be scanned, such as sweeping the scan over 16 segments (e.g., 128 receive lines in the 8×8 example). In other embodiments, the rows extend in a direction other than azimuth and are adjacent each other in a direction other than elevation.

In this scan pattern, the segments in a given row ("fast scan direction) are acquired temporally adjacent to each other. For example, 16 segments are spaced along a row. A multi-beam group of receive lines is first formed for one segment, then the next, and then the next and so on in temporal sequence along the row. Once a row is complete, the scan shifts to an adjacent row. The segments within the adjacent row are acquired in temporal sequence. The segments from different rows (e.g., segment 1 of each row) are adjacent each other, but acquired with temporal gaps ("slow scan direction"). For example, segment 1 of row 2 is acquired 16 segments later than adjacent segment 1 of row 1. Conversely, segment 2 of row 2 is acquired immediately after segment 1 of row 2 with no intervening segment acquisition. In the azimuth and elevation spaced segment example, each beam group acquired for all azimuth locations is defined as a "sweep". The "sweep" is a slab of acquired information, essentially with each collection of lines in a beam group acquired at the same time. Adjacent beam groups in the slab are acquired very close together in time (order of 200-300 microseconds). A greater temporal separation (e.g., non-adjacent times) occurs for adjacent beam groups for different sweeps of different elevation spaced slabs.

Motion causes artifacts in the ultrasound data acquired by scanning the volume. The motion is due to breathing, transducer motion, or other patient motion. Breathing may produce motion velocities on the order of 5 cm/sec. For example, a 10 cm field of view acquired in 200 msec (5 Hz) may experience a differential shift of 1 cm from one end of a volume to the other (e.g., across elevation) compared to the acquisition of a stationary field. Depending on the direction of motion, objects could experience up to a 10% dilation or compression. For example, objects moving in the positive Z-direction (in elevation) appear to be stretched out by 10% in the Z-dimension. Objects moving in the opposite direction will be shorter by 10%. Due to temporal gaps, the anatomy shifts such that the segment being scanned is not ideal.

Figure 2:
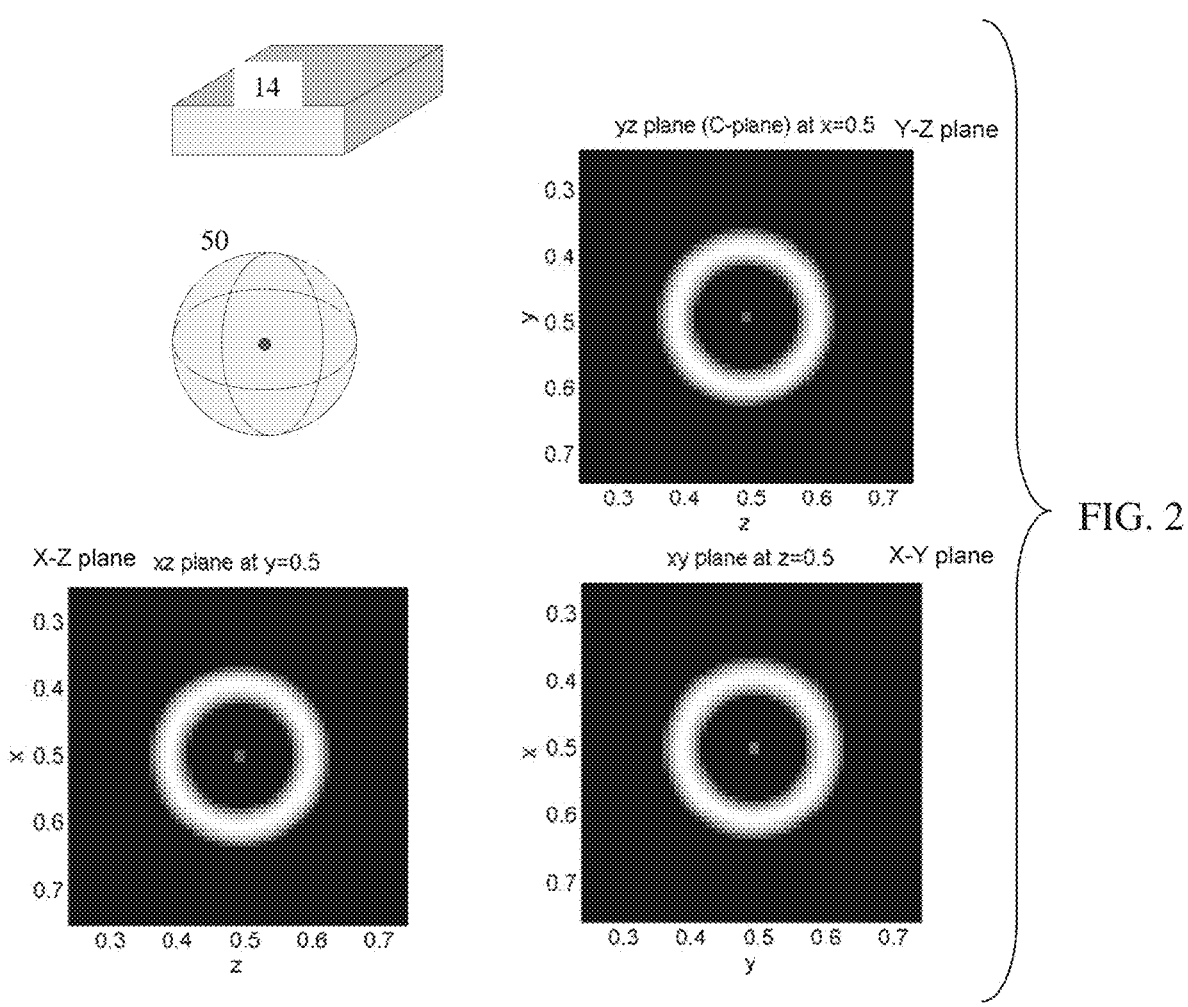
FIG. 2 illustrates an example of volume scanning, without motion, of a sphere in different planes.

FIG. 2 shows an ideal or desired scan without motion while FIGS. 3-6 represent the artifact caused by motion and the scan pattern. FIG. 2 is an example situation with a 2D array 14 interrogating a single spherical object 50. The three images show orthogonal slices thru the frame of data in the x-y, x-z and y-z (commonly referred to as the c-plane) planes, where x is range or depth, y is azimuth, and z is elevation. x, y, and z may not align with the transducer elements, so may represent other axes. In another approach, x is depth regardless of the shape of the array 14 or alignment of elements. y and z are orthogonal axes to x regardless of the array configuration where y and z are labeled as azimuth and elevation. The volumes in this example are 64×64×64 samples. The multi-beam group size in this example is 8 azimuth lines by 8 elevation lines. The volume is scanned in 8×8 azimuth, elevation scan line segments where each segment and corresponding scan lines cover the entire range of depths, 1-64. The scan pattern is along each row in azimuth over 8 segments. Each row is scanned in an azimuth sweep in sequence until 8 rows of segments have been scanned. Other size volumes, multi-beam group size, or scan patterns may be used.

Figure 3:
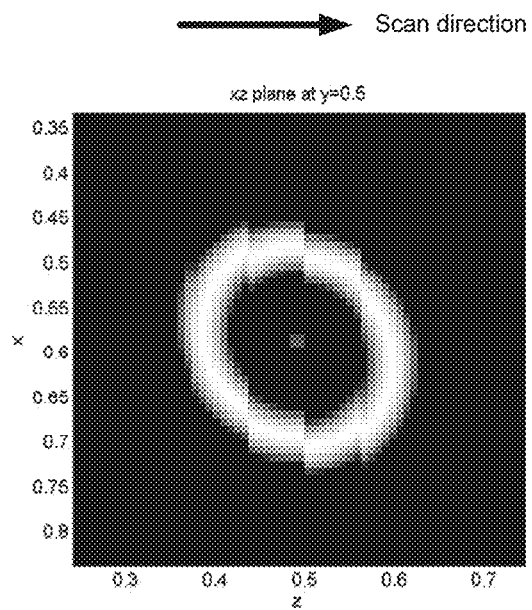
FIG. 3 shows an example of distortion in an xy plane due to motion in combination with the scanning pattern.
Figure 4:
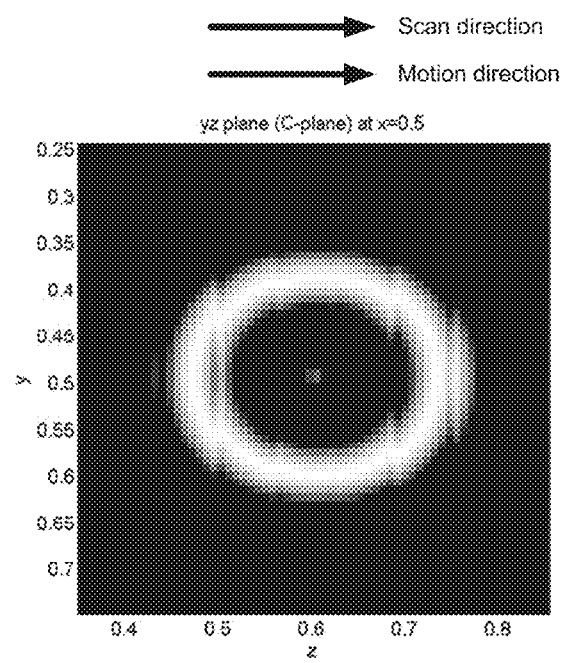
FIG. 4 shows an example of distortion in an yz plane due to motion in one direction in combination with the scanning pattern.
Figure 5:
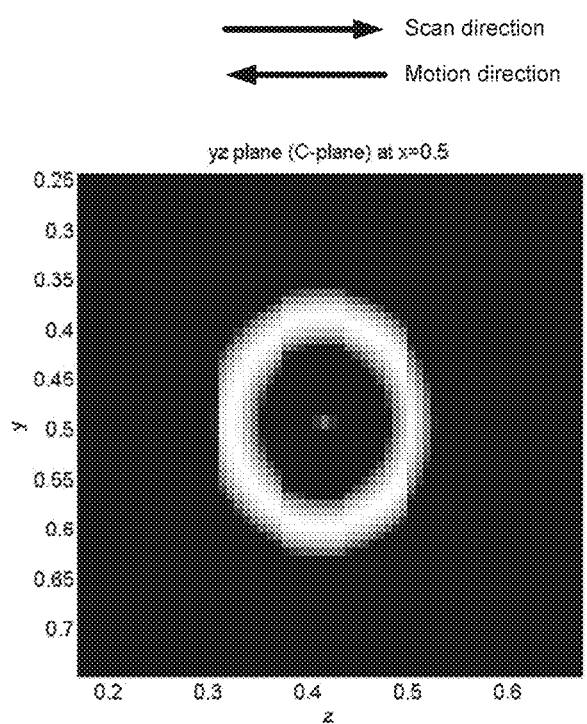
FIG. 5 shows an example of distortion in an yz plane due to motion in another direction combination with the scanning pattern.

Because of the large temporal discontinuity between adjacent elevation beam groups, moving objects exhibit geometric distortion between the groups or segments where no or little geometric distortion is within the groups of scan lines of a segment. This produces a stair-step artifact in the image plane slices (rows). FIG. 3 shows motion in the +X direction and the artifact produced by the temporal mismatch between adjacent elevation beam groups. FIGS. 4 and 5 show motion in the + and −Z directions, either with or against the elevation scan direction. For FIGS. 3-5, the translation or total magnitude of motion is 20% of the full field of view in frame acquisition period.

FIG. 3 shows the segments displaced along the x dimension from each other. This displacement may be corrected by shifting the segments along the x direction. Similarly, shifts along the y dimension may be corrected by shifting. Motion in the x or y dimension causes the segments to have to be translated relative to one another to achieve registration.

FIGS. 4 and 5 shows the segments displaced along the z direction. These shifts cause contraction or dilation. Motion in the z-direction causes the segments to have to be spaced out or overlapped. Simple registration may not result in correcting the volume. Data may be missing in gaps or more than one value may be provided in overlap. Even after shifting, data may not be provided for the end of the volume. The anatomy may move such that some of the same anatomy is scanned in each elevation spaced segment, resulting the scanned volume being for less of the anatomy than desired.

Figure 6:
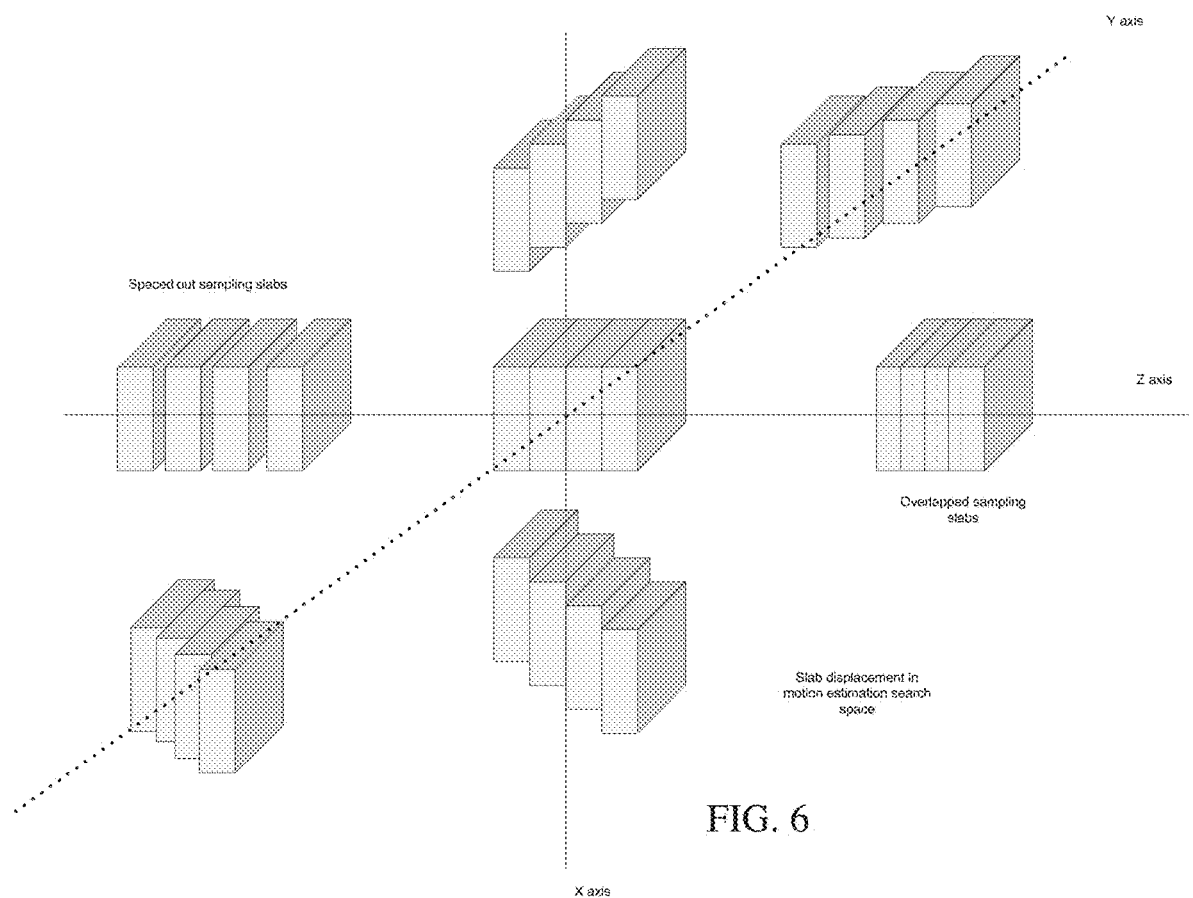
FIG. 6 graphically illustrates scanning block distortions due to motion in different directions.

FIG. 6 illustrates segments and relative positioning along the x, y, and z dimensions due to motion in combination with the scan pattern. The segments are shown along positive and negative portions of the axes to represent different directions of motion. The axes represent motion along the axes. The resulting shift is shown by the example four segments along that part of the axis. More complex translational motion in two or more axes results in corrections which require a combination of translations in the x and y dimensions and contraction or expansion in the z dimension.

The motion artifact may be corrected, in part, by motion tracking. For motion tracking, a reference is obtained in act 31 (see FIG. 1). The reference indicates the ideal or desired anatomy. In the example of FIG. 2, the reference is the sphere 50. The reference may be a template. In another embodiment, the reference is ultrasound data representing the volume in a different patient. In yet another embodiment, the reference is ultrasound data representing the volume in the same patient. For example, the volume scan is performed with the patient holding their breath and the transducer held steady during the single or multiple volume scan. This frame or combination of frames of data is used as a reference. As another example, a motion corrected frame from a previous scan is used as a reference for a subsequent scan.

In act 32, motion tracking is performed using the frame from the scan to be motion corrected and the reference. A block of ultrasound data is acquired for each of the scanned segments. In the 8×8 collection of segments for the whole volume example, 64 blocks of ultrasound data are obtained. Different blocks represent different segments or sub-volumes. Due to the scan pattern, adjacent blocks in azimuth are acquired temporally adjacent to each other. Also due to the scan pattern, adjacent blocks in elevation are acquired with different timing, such as not temporally adjacent since 7 other segments are acquired in between temporally.

The blocks of ultrasound data are corrected to reconstruct the scanned volume. The blocks of ultrasound data are motion corrected using motion tracking. The amount of adjustment of the segments depends on the anticipated level of motion, which is a function of a trial displacement. A correlation or spatial registration between each segment and the reference is performed in different tests to identify the best registration.

The registration is between frames for a given segment. The registration is performed between data for the same segment. The location of a given segment is found in the reference. The registration is a one, two, or three-dimensional registration with or without rotation and/or scaling. In one embodiment, translation without rotation is found. By determining translation in different segments or for different blocks, a rotation of the volume is determined or is dealt with or without searching for rotation of each block.

Registration is any now known or later developed motion tracking or similarity measure. Data is correlated. For example, a minimum sum of absolute differences, other sum of absolute differences, cross-correlation, or auto-correlation is used. Any now known or later developed motion correction or tracking algorithm may be used. The search in 3D space may be likened to finding where a small cube of image data has moved from the reference image to the measurement image. A sum of absolute differences (SAD) between the displaced reference image region of interest (ROI) and the measurement image ROI (e.g., block) is computed for a number of possible x, y, and z trial displacements. The trial displacement which provides the smallest SAD value is the best estimate of the actual displacement.

The similarity is measured between the block and the entire frame of the reference or a sub-set. For example, a window from a reference frame is compared to a given block. The window is a search region, larger than the block, centered on the expected location of the block relative to the reference.

A best match between frames is found. The best match indicates an offset translation, rotation, and/or scale. By testing different possible translations, rotations, and/or scales of the block relative to the reference, the offset caused by the motion is found. The registration indicates a level of transducer movement, patient movement, organ movement, combinations thereof, or other motion. Global or local motion may be determined. The best match for each of the blocks is determined.

In one embodiment, the registration relates to or is derived from the same type of data to be used for parametric imaging (e.g., contrast agent response). In another embodiment, characteristics of at least a first type of data (e.g., B-mode) are used for the registering, and data of at least a second type of data is used for perfusion analysis. For example, several clinical ultrasound images or frames of data with mixed contrast agent type data and B-mode type data are used—the B-mode or more tissue responsive data used for registration and the contrast agent or more contrast agent responsive data used for perfusion study.

Once the offset is determined, the spatial location represented by the block of ultrasound data is adjusted. The locations of data obtained by the multi-beam groups are set based on the correlating. The ultrasound data is shifted using the offset. The estimated displacement is used to affect registration between the reference image and the measurement image. This adjustment causes the same locations to align over time despite motion.

Referring to FIG. 3, the motion correction realigns the segments. The adjacent multi-beam groups within the rows are spatially registered to the reference, so are re-aligned. In the case of linear motion in the X or Y dimension, only displacement of the blocks is tested.

Figure 7:
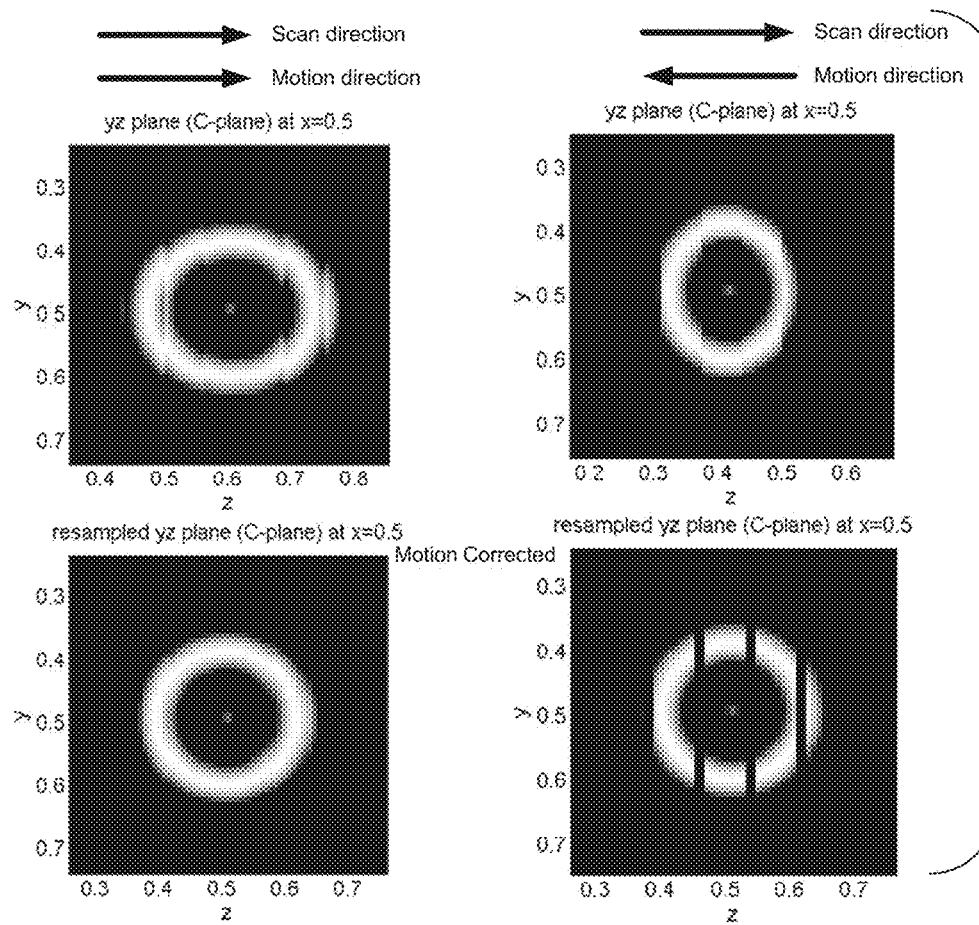
FIG. 7 shows examples of contraction and dilation motion artifact reduction by re-sampling.

For linear motion in the z direction, the position of each of the blocks in the z dimension is adjusted, resulting in gaps between the blocks for motion in the elevation scan direction or in overlap for motion against the elevation scan direction. FIG. 7 represents the effects of motion correction in the z direction. For the upper left image, motion causes the segments to separate from each other. This dilates the volume. For the upper right image, motion causes the segments to overlap. This contracts the volume. The motion registration counteracts the dilation and contraction, as shown by the lower images. The correction itself causes image artifacts. Expanding out the overlap results in gaps. Contracting the dilation results in multiple data for a same voxel.

In act 34, a correction is performed for the timing being different in the elevation direction as compared to the azimuth direction for the adjacent blocks. The correction accounts for the artifact remaining after motion correction. The correction to account for the scan pattern timing artifact after motion correction is applied prior to or after the motion correction. Any correction may be used. Act 36 and acts 38, 40 represent different embodiments of the correction.

In the embodiment represented by act 36, re-sampling along the z-axis is applied. To account for contraction or dilation in the calculation of parametric information, the results of the spatial registration are used. The overlap for the volume scan caused by motion and subsequent motion correction is identified.

The spatial registration may result in the contraction of represented locations of the ultrasound data from the scanning relative to the volume. Below is an example of a block resequencing pattern for contraction by 20% with an elevation beam group size again of 8 lines. The read lines in groups of 8 correspond to blocks where each numerical value is of a scan line. Lines 1-8 are one block, lines 9-16 another block, and so on. The output line is the 64 scan lines of the final volume and/or the volume being scanned without any motion artifact.

```
Output Line:   1 2 3 4 5 6 7 8 9 10 11 12 13 14 15 16 17 18 19 20 21 22 23 24
Read Line1:    1 2 3 4 5 6 7 8                17 18 19 20 21 22 23 24
Read Line2:                  9 10 11 12 13 14 1516                   25 26 27 28
25 26 27 28 29 30 31 32 33 34 35 36 37 38 39 40 41 42 43 44 45 46 47 48
           33 34 35 36 37 38 39 40               49 50 51 52 53 54 55 56
29 39 31 32                  41 42 43 44 45 46 47 48                 57 58
49 50 51 52 53 54 55 56 57 58 59 60 61 62 63 64
59 60 61 62 63 64 x x x x x x x x x x
```

The blocks overlap after spatial registration, resulting in data not being acquired for edge volume locations due to motion. This is represented by "x". The correction deals with both the overlap and the missing information due to contraction.

The overlap is accounted for by combining or selecting data to be used in an overlap location. For a voxel represented by data from different blocks after motion correction (e.g., output line 8 is represented by data from receive scan line 8 and receive scan line 10), the different values are used. For example, the data is averaged. As another example, one of the values is selected based on a comparison of the possible values (e.g., select the highest, lowest, or value most similar to adjacent non-overlap values). The data from both blocks is used in the correction. In the selection option, the data from both is used to provide for the selection. For large amounts of contraction, more than two blocks may be combined for some of the output lines.

The contraction has left no data at the end of the volume (e.g., denoted again by 'x'). Zeros may be inserted in these missing data regions to indicate that there is no information available. The re-sampling may shift the volume to distribute some of the missing data to the start of the volume so that the center of the volume experiences zero net displacement. Alternatively, data from the reference or other frame with data available for those locations (e.g., temporally nearest frame) replaces the x or missing information. In another alternative, the data is determined by extrapolation.

Where motion causes expansion, the gaps are identified. The spatial registration results in the dilation of represented locations of the ultrasound data from the scanning relative to the volume. Below is an example of a slab re-sequencing pattern for expansion by 20% with an elevation beam group size of 8 lines acquiring a total of 64 elevation lines. The 'x' again denotes that there is missing information. In this case, the missing information is in the gaps.

```
Output Line:  1 2 3 4 5 6 7 8 9 10 11 12 13 14 15 16 17 18 19 20 21 22 23 24
Read Line:    1 2 3 4 5 6 7 8 x x  9 10 11 12 13 14 15 16 x  x  17 18 19 20
25 26 27 28 29 30 31 32 33 34 35 36 37 38 39 40 41 42 43 44 45 46 47 48
21 22 23 24 x  x  25 26 27 28 29 30 31 32 x  x  33 34 35 36 37 38 39 40
49 50 51 52 53 54 55 56 57 58 59 60 61 62 63 64
x  x  41 42 43 44 45 46 47 48 x  x  49 50 51 52
```

The gap, which exists despite motion correction, is dealt with. To account for the gap, replacement data is provided in the gap. The replacement data may be from a temporally adjacent or temporally nearest frame with information for those locations. Interpolation may be used, such as interpolating from voxels of adjacent scan lines for which data is available.

In another approach, parametric or other calculating is prevented for the gap locations caused by the dilation. Zeros or other indicators of missing data are inserted for subsequent processing. Parametric imaging is adjusted to ignore the gaps when computing parameters, such as the maximum intensity projection (MIP) or arrival time over many frames. Since the parameters are calculated over time, the missing data may not be needed. Parameters that are created from fitting curves to a time-intensity graph may ignore this missing data as the curve fitting may still be performed. The curve fitting indicates the values for the gap. Alternatively, parameter values are not calculated for the masked or unavailable locations.

FIG. 6 and the discussion above are in the context of data in a Cartesian coordinate system. In a non-Cartesian acquisition grid (e.g., polar), the segments are non-rectangular. This change does not alter the motion artifact. The same process may be used.

Within a block, the samples are not adjusted relative to each other. The adjustment positions the locations of the block within the registration, reference, or output grid. The grid may change to account for the adjustment in the re-sampling.

With very large amounts of motion, the blocks are curved in the y-dimension before combining with other blocks since there is a significant time between the first and last azimuth lines of a sweep or row. Any now known or later developed non-rigid spatial transform may be used to account for motion distortion. When the motion contains rotational components, then the motion correction applied to the position of individual blocks is adjusted for rotation. More complex motion that is not uniform in the field of view may be corrected on a regional basis.

In act 38, the scan pattern artifact in motion correction is corrected for by alignment. The volume scan pattern is aligned to a direction of motion. In act 40, the direction of movement of the anatomy within the patient is detected. The predominant direction of periodic motion (i.e. breathing) in a volumetric image is determined by conventional motion tracking or by otherwise determining the anatomical orientation. Ultrasound examination may be used. For example, a small volume or orthogonal planes are scanned. Using motion tracking or other correlation, the direction of the motion in three-dimensions is determined. For breathing motion, the direction is primarily along one vector. The direction of the vector is found in three dimensions. In other embodiments, the direction is determined based on the position of the transducer relative to the patient. The direction of breathing movement relative to the liver or other organs is along the long axis of the patient. Knowing the transducer position relative to the patient indicates the direction of motion within the scanned volume.

The scan pattern is aligned in act 38 based on the direction of motion. The rows or azimuth direction is aligned to be the same as the direction of motion or the direction of the greatest magnitude of motion. The azimuth is set to be substantially parallel to the direction of movement. "Substantially" is used to account for the acceptance angle of the transducer limiting alignment. The scan sequence is adjusted so that the fast time scan dimensions (x and y) are oriented in the motion direction. The slow time scan dimension is oriented substantially perpendicular to the motion such that motion will only cause relative displacement of the slabs without producing gaps or overlap between slabs. This may improve reconstructed image quality within the center of the field of view of the volume and simplify the reconstruction process.

The motion registration is performed as well as the alignment. The corrections to account for gaps and overlap may be avoided.

In act 42, parametric information is calculated. The scanning provides a sequence of ultrasound frames. The frames are corrected for motion and the effects of the scan pattern on the correction are accounted for. The result is data representing multiple locations within the volume of the patient over time. A parameter may be calculated for one or more of the locations using the information over time. Alternatively or additionally, spatial parameters are calculated.

For contrast agent imaging, the perfusion quantity may be a function of the data distributed along three spatial dimensions in the three-dimensional region, a function of data for one location, a function of one-dimensional distribution of data, or a function of a two-dimensional distribution of data. Information from frames is combined. The combination is for any now known or later developed inter-frame processing, such as maximum intensity holding, minimum intensity holding, mean determination, or constructing one or more time intensity curves. Parameter data for the volume is generated as a function of data from the frames. The selected frames of ultrasound data are integrated as a function of time to determine the parameter values for each location. Integrated includes mathematical integration or forming an image from a plurality of sources.

For each spatial location of a region of interest, the data is compared or used to determine a value. For each voxel, a value is selected as a function of data from each of the frames of data. For example, the mean, median or other statistical value of data for each spatial location as a function of time is determined from the frames. As another example, the maximum, minimum, or other data in relation to data of the selected frames is selected based on comparison. The frames of the selected subset are combined into a persisted frame or single frame. In another example, a curve representing intensity or other contrast agent response as a function of time is determined from the frames. The curve is for a region or for a spatial location. Since the frames are associated with different times, the curve is of intensity as a function of time. A characteristic of the curve may be determined as the parameter.

In one embodiment, the parameter is a characteristic of perfusion. The time to maximum wash-in, the time for wash-out, or other characteristic of the perfusion is calculated. A curve may be fit to the data for the calculation. Alternatively, the data is used as samples without the curve fitting to find the characteristic. In yet another example, a time for sufficient contrast agent response to return to the spatial location is calculated.

In other embodiments, the motion corrected and artifact reduced frames of data are used for other purposes instead of or in addition to parametric imaging. For example, one or more frames may be used to spatially and/or temporally register with data from other modes of examining or imaging the patient. CT or MR volumetric data may be registered with the ultrasound frame or frames.

In act 44, an image is displayed. The image is a function of the ultrasound data after correction for the motion and scan pattern artifact. In one embodiment, the image is rendered from the frame or frames of data representing the volume. In another embodiment, the image is rendered from parametric values calculated from the frames. A parametric image is generated, such as a wash-in or wash-out image. The parametric values and/or other values are used. For example, the parameter (quantity) for each spatial location in the volume (i.e., each voxel) is used for rendering. Surface or projection rendering may be used. For projection rendering, maximum, minimum, averaging or other projection may be used. Alpha blending may be used. The rendering of the volume may be with or without opacity weighting and/or shading. Any now known or later developed rendering of the volume may be used. In alternative embodiments, a cut-plane image or multi-planar reconstruction images are generated from the reperfusion data of the volume.

The image may represent a maximum return from contrast agents over the sequence period or other parameter of perfusion. The perfusion parameter information is used as voxel data for rendering the image. The image is a rendering with pixels modulated as a function of a perfusion level for the portion of the region represented by the respective pixel. The perfusion rendering may be viewed alone or separately. Alternatively, the perfusion information is overlaid or blended with a rendering from other data, such as tissue (e.g., B-mode) or flow (e.g., Doppler velocity or energy).

In an alternative or additional embodiment, a quantity is displayed. The quantity is a number or text, such as "1.4 seconds." A graph, such as average contrast agent in a region as a function of time, may be displayed. One or more time-intensity curves may be displayed, such as different curves derived from local averages at different regions in the volume.

Figure 8:
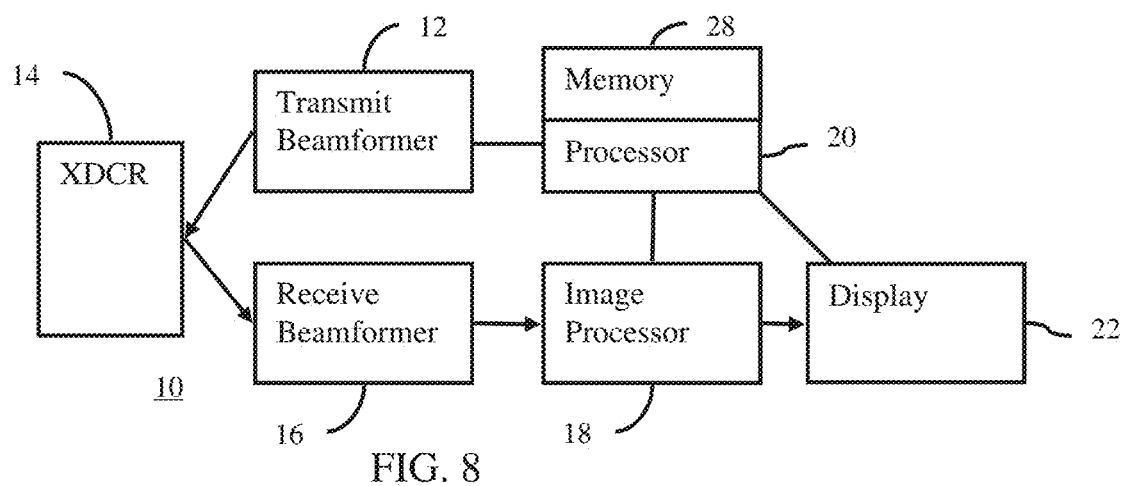
FIG. 8 is a block diagram of one embodiment of an ultrasound imaging system for motion artifact suppression for three-dimensional parametric ultrasound imaging.

FIG. 8 shows a system 10 for motion artifact suppression for three-dimensional parametric ultrasound imaging. The system 10 includes a transmit beamformer 12, a transducer 14, a receive beamformer 16, an image processor 18, a control processor 20, a display 22, and a memory 28. Additional, different, or fewer components may be provided. For example, a separate memory is provided for buffering or storing frames of data over time. As another example, the control processor 20 is combined with or part of the image processor 18. The control processor 20 may be separate processors, such as one for controlling scanning and another for rendering an image.

The system 10 is a medical diagnostic ultrasound imaging system in one embodiment, but other imaging systems of the same (ultrasound) or different modality may be used. In other embodiments, part or all of the system 10 is implemented in a computer or workstation. For example, previously acquired frames of data are processed without the beamformers 12, 16 or transducer 14.

The transmit beamformer 12 is an ultrasound transmitter, memory, pulser, analog circuit, digital circuit, or combinations thereof. The transmit beamformer 12 is operable and configured to generate waveforms for a plurality of channels with different or relative amplitudes, delays, and/or phasing. Upon transmission of acoustic waves from the transducer 14 in response to the generated waves, one or more beams are formed. The transmit beamformer 12 may cause the beam to have a particular phase and/or amplitude. For example, the transmit beamformer 12 transmits a sequence of pulses associated with a given scan line or to adjacent scan lines. The pulses correspond to beams with different amplitudes and/or relative phases. In alternative embodiments, a single beam is used for any given scan line and/or beams with a same amplitude and/or relative phases are used. The beam may be focused, unfocused, or have an infinite focus. Any broad beam for insonifying multiple receive scan lines may be generated.

The transducer 14 is a 1-, 1.25-, 1.5-, 1.75- or 2-dimensional array of piezoelectric or capacitive membrane elements. Two-dimensional arrays provide electronic steering in azimuth and elevation with or without equal numbers of elements along both dimensions. The two-dimensional array may be flat or curved. The transducer 14 includes a plurality of elements for transducing between acoustic and electrical energies. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. Using a memory and/or channels, more than one receive beam may be generated. Different delay profiles and/or apodization are applied to the same signals to generate receive beams simultaneously or in response to the same receive data. For example, a parallel beamformer is provided for forming 4-64 beams in response to a given transmit event. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

Any desired sequence of transmit and receive operation may be used to obtain ultrasound information. For example, B-mode data may be obtained by scanning a line once. The B-mode may be used for tissue imaging. Correlation or motion tracking may be used to derive fluid information from B-mode data. B-mode operation may provide contrast agent information. Doppler information may be obtained by transmitting sequences of beams along each scan line. A corner turning memory may be used to isolate tissue, contrast agents, and/or flow information from Doppler signals. Other now known or later developed modes may be used.

In one embodiment, the mode is a contrast agent imaging mode. Contrast agents may be imaged with typical B-mode or Doppler techniques. Isolating information at the second, even, odd, sub, or other harmonics may more likely identify information from contrast agents. For example, a two pulse technique is used. The pulses have a same amplitude, but different phase. By summing the response, information associated with even harmonics is identified. Filtering may alternatively be used. Alternatively or additionally, relative phasing is provided in the receive processing.

In one embodiment, the transmit sequence is controlled to generate echo signals responsive to the cubic fundamental. The beamformer 12 is operable to transmit a plurality of pulses having at least two different amplitude levels and at least two of the plurality of pulses having opposite or different phases. Transmitter power can be varied in any suitable manner, as for example by adjusting the voltage applied to individual transducer elements, or by adjusting the number of transducer elements (or transmit aperture) used to form a particular pulse.

For obtaining ultrasound data at the cubic fundamental, the receive beamformer 16 includes line memories and a summer or a filter to combine signals responsive to the transmissions. The line memories or buffers can be formed as physically separate memories, or alternately they can be formed as selected locations in a common physical device. The beamformed signals are stored in the line memories or buffers and then weighted and summed in a weighted summer. Weighting values for both amplitude and phase are used in the weighted summer. The memories and the summer can be implemented using analog or digital techniques. The weighted summer forms a composite output signal by weighting the separate beamformed receive signals. The composite output signal for a given spatial location is a sample associated with the cubic fundamental response.

Obtaining cubic fundamental information is disclosed in U.S. Pat. No. 6,494,841, the disclosure of which is incorporated herein by reference. Any of the transmit sequences and receive combinations disclosed therein may be used for obtaining cubic fundamental information. Other transmit sequences and receive combinations for obtaining cubic fundamental information may be used, such as disclosed in U.S. Pat. Nos. 6,602,195, 6,632,177, 6,638,228 and 6,682,482, the disclosures of which are incorporated herein by reference. In general, a sequence of pulses with different amplitudes and phases are transmitted. Using amplitude change or different amplitudes without different phases may also be used to obtain cubic fundamental information. By combining received signals responsive to the sequence, a sample including cubic fundamental information is obtained. The cubic fundamental information is highly specific to ultrasound contrast agents since contrast agents produce cubic response and the transducer and tissue produce very little cubic response. The information provides tissue clutter rejection, allowing for imaging more specific to contrast agents. For example, small vessels within tissue may be more easily imaged or identified using cubic fundamental information.

The transmit beamformer 12 and receive beamformer 16 are configured to scan a volume. Each transmission illuminates a segment for forming multiple receive beams. The echoes from the transmission are used to generate the receive beams. The scanning sweeps in a pattern to scan the volume in the multi-beam groups. Any pattern may be used, such as scanning or sweeping the multi-beam groups along one direction (e.g., azimuth), and then repeating along the same direction but spaced in a slab along an orthogonal direction (e.g., sweeping parallel slabs spaced in elevation).

The image processor 18 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for detecting information for display from beamformed ultrasound samples.

In one embodiment, the image processor 18 implements a fast Fourier transform from a plurality of samples representing a same region or gate location. Each of the samples is responsive to cubic fundamental so that a pulsed wave Doppler display may be generated from cubic fundamental information. The image processor 18 also includes a B-mode detector in a parallel track. The B-mode detector operates on the same or different beamformed samples to detect tissue, contrast agent, or tissue and contrast agent response. For example, one receive beam for each spatial location from the sequence of receive beams used for cubic fundamental isolation is applied to the B-mode detector for imaging primarily tissue information.

The image processor 18 outputs frames of ultrasound data. The frames of data are formatted in an acquisition format (e.g., polar coordinate), a display format (e.g., scan converted into a Cartesian coordinate format or an image), or other format. Each frame of data represents a three-dimensional scanned region. The frames of data include a single or multiple types of data. For example, one frame of data includes just contrast agent information. As another example, one frame of data includes contrast agent information for some spatial locations and another type of information (e.g., B-mode or Doppler) for other spatial locations. Different types of data may be provided in the same frame for a same spatial location. In another example, the different types of data are provided in different frames of data.

In an alternative embodiment, the image processor 18 loads data from a network or memory. For example, DICOM or other data sets are loaded. Each data set is a frame of data. One frame may include different types of data, one overlaid on another. Alternatively, each frame includes only one type of data with different frames for different data types. In another embodiment, each frame is subdivided so that one portion includes one type of data and another portion includes another type of data.

The control processor 20 is an application specific integrated circuit, correlation processor, Fourier transform processor, general processor, control processor, field programmable gate array, digital signal processor, analog circuit, digital circuit, graphic processing unit, combinations thereof, or other now known or later developed device for determining similarity and/or displacement between frames of data. The control processor 20 controls operation of the transmit and receive beamformers 12, 16, the image processor 18, and/or the display 22. For example, the control processor 20 causes the transmit beamformer 12 and receive beamformer 16 to align the scan pattern with a direction of motion. The direction of motion is input by the user, determined by the image processor 18, and/or determined by the control processor 20.

The control processor 20 or the image processor 18 performs motion correction. The motion correction may also include accounting for the interaction of the scan pattern with the motion. For example, the image processor 18 re-samples data for outputting a frame. The re-sampling includes inserting zeros, blocking calculation for gaps, creating or selecting information to fill gaps, combining or selecting data for overlap, or other processing to account for dilation or contraction.

The control processor 20 or image processor 18 may calculate one or more values for parameters, such as contrast agent perfusion parameters. The control processor 20 or image processor 18 may also include a rendering processor, graphics processing unit, alpha blending buffer, other buffer, memory, processor, adder, or other device for generating an image from information of a volume set of data or reperfusion parameter values. An image, such as a parametric image, representing a volume is rendered.

The display 22 is a CRT, monitor, LCD, flat panel, projector or other display device. The display 22 receives display values for displaying an image. The display values are formatted as a three-dimensional representation. In one embodiment, the display values are for an image generated as a function of frames of data acquired at different times. As additional frames of data are acquired and selected, the image may be updated. Other images, such as images from single or component frames of data, may also be displayed.

The display 22 may display an image rendered from perfusion information in three-dimensions. The perfusion information is determined by local destruction and reperfusion measurements. The data is rendered to represent reperfusion for the volume from a selected viewing angle or arbitrary cut-plane.

The image processor 18 and/or control processor 20 operate pursuant to instructions. A computer readable storage medium, such as the memory 28, stores data representing instructions executable by one or both of these programmed processors for motion artifact suppression for three-dimensional parametric ultrasound imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The memory 28 may alternatively or additionally store ultrasound data, direction information, parameter values, scan pattern information or other information used for motion artifact suppression for three-dimensional parametric ultrasound imaging. Other memories, such as buffers or CINE memory may be used for storing data.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A non-transitory computer readable storage medium having stored therein data representing instructions executable by a programmed processor for motion artifact suppression for three-dimensional parametric ultrasound imaging, the storage medium comprising instructions for:

motion tracking for blocks of ultrasound data acquired with multiple beam reception in a volume scan, the blocks being spaced in a first direction and being spaced in a second direction different than the first direction, timing of the volume scan being different for the blocks as spaced in the first direction than for the blocks as spaced in the second direction, the motion tracking being block-by-block of each of the blocks with a reference data set;

adjusting spatial positions of the blocks with respect to each other based on the motion tracking, the adjusting of the spatial positions resulting in block-based spatial separation or block-based spatial overlap of the blocks due to the timing being different for the blocks spaced in the second direction as compared to the first direction;

correcting the block-based spatial separation or the block-based spatial overlap of the blocks; and displaying a parametric image, the image being a function of the blocks of the ultrasound data with the adjusted spatial positions and after the correcting.

2. The non-transitory computer readable storage medium of claim 1 wherein motion tracking comprises registering each of the blocks of ultrasound data to the reference data set.

3. The non-transitory computer readable storage medium of claim 1 wherein the first direction comprises an azimuth direction and the blocks along the azimuth direction are acquired in temporal sequence, and wherein the second direction comprises an elevation direction and the blocks along the elevation direction are acquired with temporal gaps.

4. The non-transitory computer readable storage medium of claim 3 wherein correcting comprises aligning the first direction as an azimuth scan direction in a pattern of the scanning of the volume scan with a direction of motion from the motion tracking.

5. The non-transitory computer readable storage medium of claim 1 wherein correcting comprises re-sampling along the second direction.

6. The non-transitory computer readable storage medium of claim 1 wherein correcting comprises accounting for a gap of the block-based spatial separation.

7. The non-transitory computer readable storage medium of claim 1 wherein correcting comprises accounting for an overlap of the block-based spatial overlap.

8. The non-transitory computer readable storage medium of claim 1 wherein correcting comprises aligning the first direction or the second direction as an azimuth or elevation scan direction in a pattern of scanning of the volume scan to a direction of motion from the motion tracking.

9. The non-transitory computer readable storage medium of claim 1 wherein the instructions further comprise an instruction for calculating parametric values for locations represented by the ultrasound data after the correcting, wherein displaying comprises displaying the parametric image based on the parametric values calculated for locations after the correcting.

10. A method for motion artifact suppression, the method comprising:
   detecting a direction of movement of anatomy within a patient;
   ultrasonically scanning, with a transducer, a volume with ultrasound in a pattern sweeping beams across each of a plurality of rows of the volume, the rows each swept in sequence, where each of the rows is swept to scan a plane, each of the rows corresponding to a different plane;
   setting a direction of the rows of the pattern during the ultrasonically scanning, the direction of the rows of the pattern and corresponding plane positions of the rows of the pattern oriented to the direction of the movement of the anatomy; and
   generating an image from data acquired by the ultrasonically scanning.

11. The method of claim 10 wherein detecting comprises detecting with ultrasound examination, wherein ultrasonically scanning comprises scanning with multi-beam receive where multi-beam groups are fired in sequence along each row in a sweep of a first direction, the rows spaced in a second direction orthogonal to the first direction, and wherein setting comprises aligning the first direction to be parallel with the direction of movement.

* * * * *